(12) United States Patent
Whitson (10) Patent No.: US 6,603,987 B2
(45) Date of Patent: Aug. 5, 2003

(54) HOLLOW MICRONEEDLE PATCH (75) Inventor: Robert C. Whitson, Goshen, IN (US)

(73) Assignee: Bayer Corporation, Elkhart, IN (US)

( * ) Notice: Subject to any disclaimer, the term of this patent is extended or adjusted under 35 U.S.C. 154(b) by 155 days.

(21) Appl. No.: 09/877,519

(22) Filed: Jun. 11, 2001

(65) Prior Publication Data

US 2002/0006355 A1 Jan. 17, 2002

Related U.S. Application Data (60) Provisional application No. 60/217,424, filed on Jul. 11, 2000.

(51) Int. Cl.[7] .......................... G01N 27/26; G01N 31/22
(52) U.S. Cl. .......................... 600/345; 600/365; 422/56; 422/58; 422/82.05; 436/169
(58) Field of Search ................................ 600/345, 347, 600/316, 317, 322, 341, 365, 367, 368, 583; 604/19–22, 506, 46, 272, 274, 307, 27; 422/56, 58, 82.05; 436/169

(56) References Cited

U.S. PATENT DOCUMENTS

| | | | | | |
|---|---|---|---|---|---|
| 5,457,041 | A | * | 10/1995 | Ginaven et al. | 435/172.1 |
| 6,091,975 | A | * | 7/2000 | Daddona et al. | 600/345 |
| 6,219,574 | B1 | * | 4/2001 | Cormier et al. | 604/20 |
| 6,256,533 | B1 | * | 7/2001 | Yuzhakov et al. | 604/21 |
| 6,334,856 | B1 | * | 1/2002 | Allen et al. | 604/191 |
| 6,379,324 | B1 | * | 4/2002 | Gartstein et al. | 604/22 |
| 6,440,096 | B1 | * | 8/2002 | Lastovich et al. | 604/27 |
| 6,501,976 | B1 | * | 12/2002 | Sohrab | 600/347 |
| 6,503,231 | B1 | * | 1/2003 | Prausnitz et al. | 604/272 |
| 2002/0155737 | A1 | * | 10/2002 | Roy et al. | 439/66 |
| 2002/0177764 | A1 | * | 11/2002 | Sohrab | 600/345 |
| 2003/0045837 | A1 | * | 3/2003 | Delmore et al. | 604/46 |

FOREIGN PATENT DOCUMENTS

WO      00/22977    *   4/2000

* cited by examiner

Primary Examiner—John A. Jeffery
(74) Attorney, Agent, or Firm—Jerome L. Jeffers (57) ABSTRACT

A test strip is provided for use in the determination of the concentration of an a chemical in blood. The test strip comprises a plurality of microneedles and a test area. Each microneedle is adapted to puncture skin and to draw blood. The test area is in fluid communication with the microneedles. The test area contains a reagent adapted to produce a reaction indicative of the concentration of the chemical in blood.

19 Claims, 10 Drawing Sheets

HOLLOW MICRONEEDLE PATCH

This application claims benefit of Provisional Application Ser. No. 60/217,424 filed Jul. 11, 2000.

FIELD OF THE INVENTION

The present invention relates generally to blood monitoring devices, and, more particularly, to a test patch for painlessly obtaining a sample of blood.

BACKGROUND OF THE INVENTION

It is often necessary to quickly and painlessly obtain a sample of blood and perform a quick analysis of the blood. One example of a need for painlessly obtaining a sample of blood is in connection with a blood glucose monitoring system where a user must frequently use the system to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and that person may eventually pass out. A person can also become very ill if their blood glucose level becomes too high—a condition known as hyperglycemia. Both conditions, hypoglycemia and hyperglycemia, are both potentially life-threatening emergencies.

Figure 1:
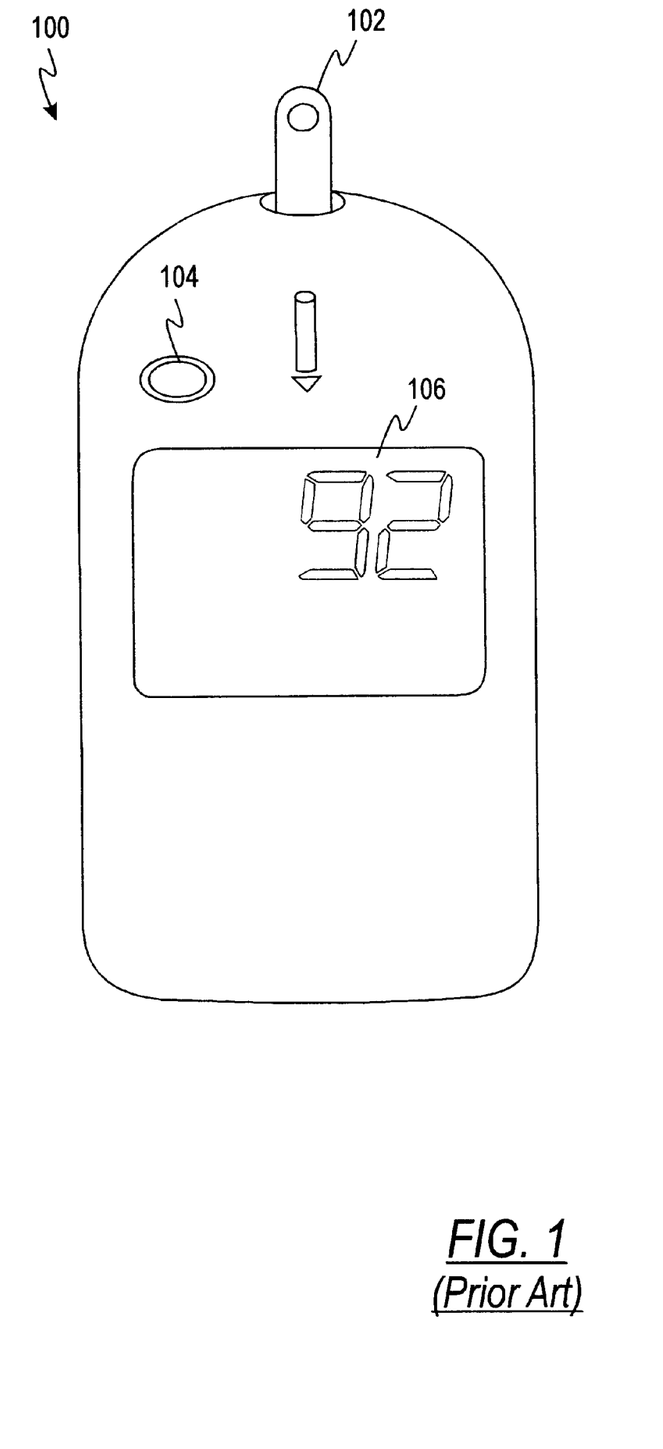
FIG. 1 is a top view of a prior art blood glucose testing device.
Figure 2:
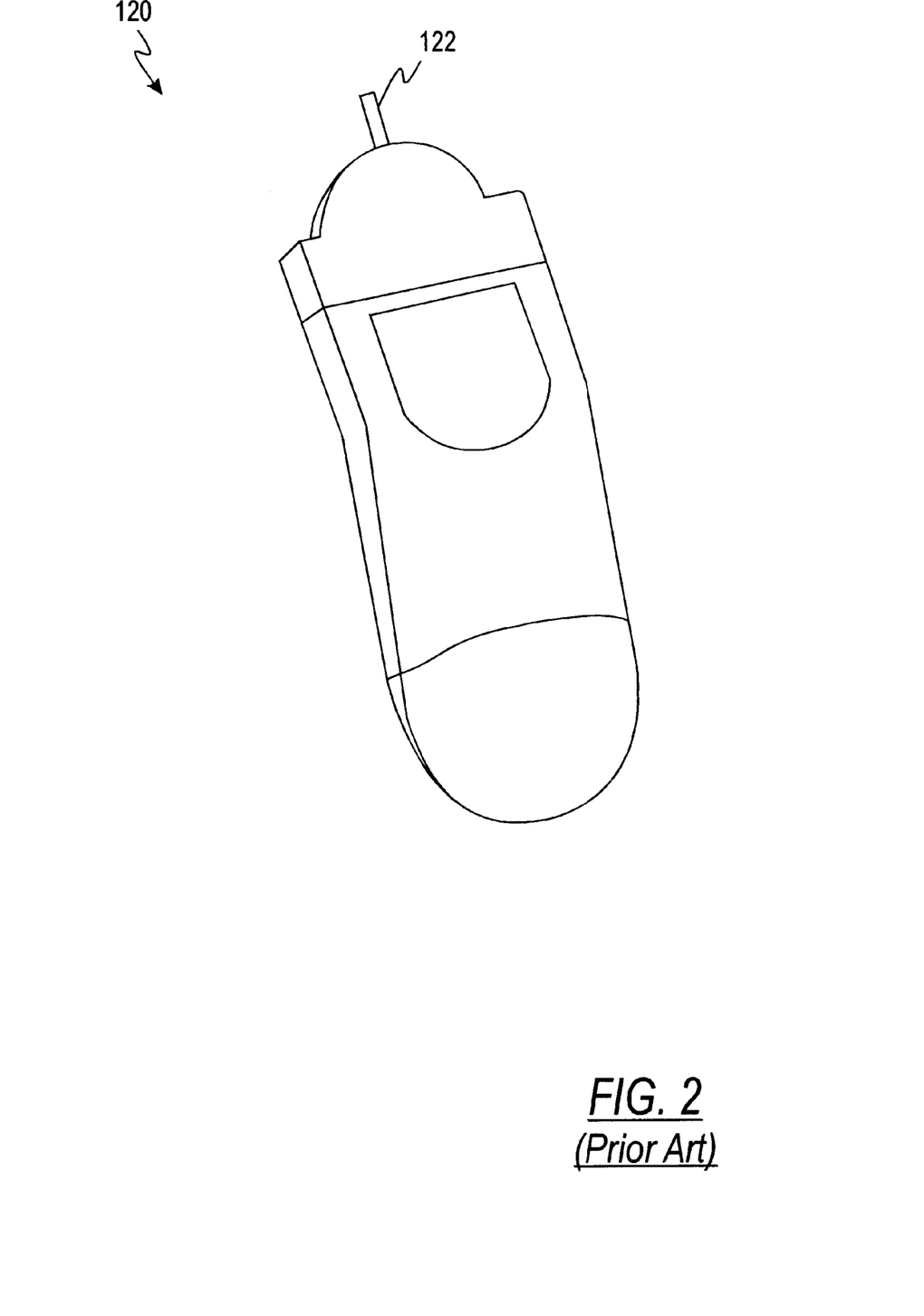
FIG. 2 is a perspective view of a prior art lance.

One method of monitoring a person's blood glucose level is with a portable, hand-held blood glucose testing device. A prior art blood glucose testing device 100 is illustrated in FIG. 1. The portable nature of these devices 100 enables the users to conveniently test their blood glucose levels wherever the user may be. The glucose testing device contains a test sensor 102 to harvest the blood for analysis. The device 100 contains a switch 104 to activate the device 100 and a display 106 to display the blood glucose analysis results. In order to check the blood glucose level, a drop of blood is obtained from the fingertip using a lancing device. A prior art lancing device 120 is illustrated in FIG. 2. The lancing device 120 contains a needle lance 122 to puncture the skin. Some lancing devices implement a vacuum to facilitate the drawing of blood. Once the requisite amount of blood is produced on the fingertip, the blood is harvested using the test sensor 102. The test sensor 102, which is inserted into a testing unit 100, is brought into contact with the blood drop. The test sensor 102 draws the blood to the inside of the test unit 100 which then determines the concentration of glucose in the blood. Once the results of the test are displayed on the display 106 of the test unit 100, the test sensor 102 is discarded. Each new test requires a new test sensor 102.

One problem associated with some conventional lancing devices is that there is a certain amount of pain associated with the lancing of a finger tip. Diabetics must regularly self-test themselves several time per day. Each test requires a separate lancing, each of which involves an instance of pain for the user.

Another problem associated with some conventional lancing devices is that the lacerations produced by the lances are larger than necessary and consequently take a greater time to heal. The greater the amount of time for the wound to heal translates into a longer period of time in which the wound is susceptible to infection.

Another problem associated with some conventional blood glucose monitoring devices is that the user's blood physically contacts the elements within the testing unit. Cross-contamination can be a problem if the monitoring device is used by more than one user such as a clinical setting.

SUMMARY OF THE INVENTION

According to one embodiment of the present invention, a test strip is provided for use in the determination of the concentration of a chemical in blood. The test strip comprises an array of microneedles and a test area. Each microneedle is adapted to puncture skin and to draw blood. The test area is in fluid communication with the microneedles. The test area contains a reagent adapted to produce a reaction indicative of the concentration of the chemical in blood.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE DRAWINGS

Other objects and advantages of the invention will become apparent upon reading the following detailed description in conjunction with the drawings in which.

DETAILED DESCRIPTION OF THE PREFERRED EMBODIMENTS

Figure 3:
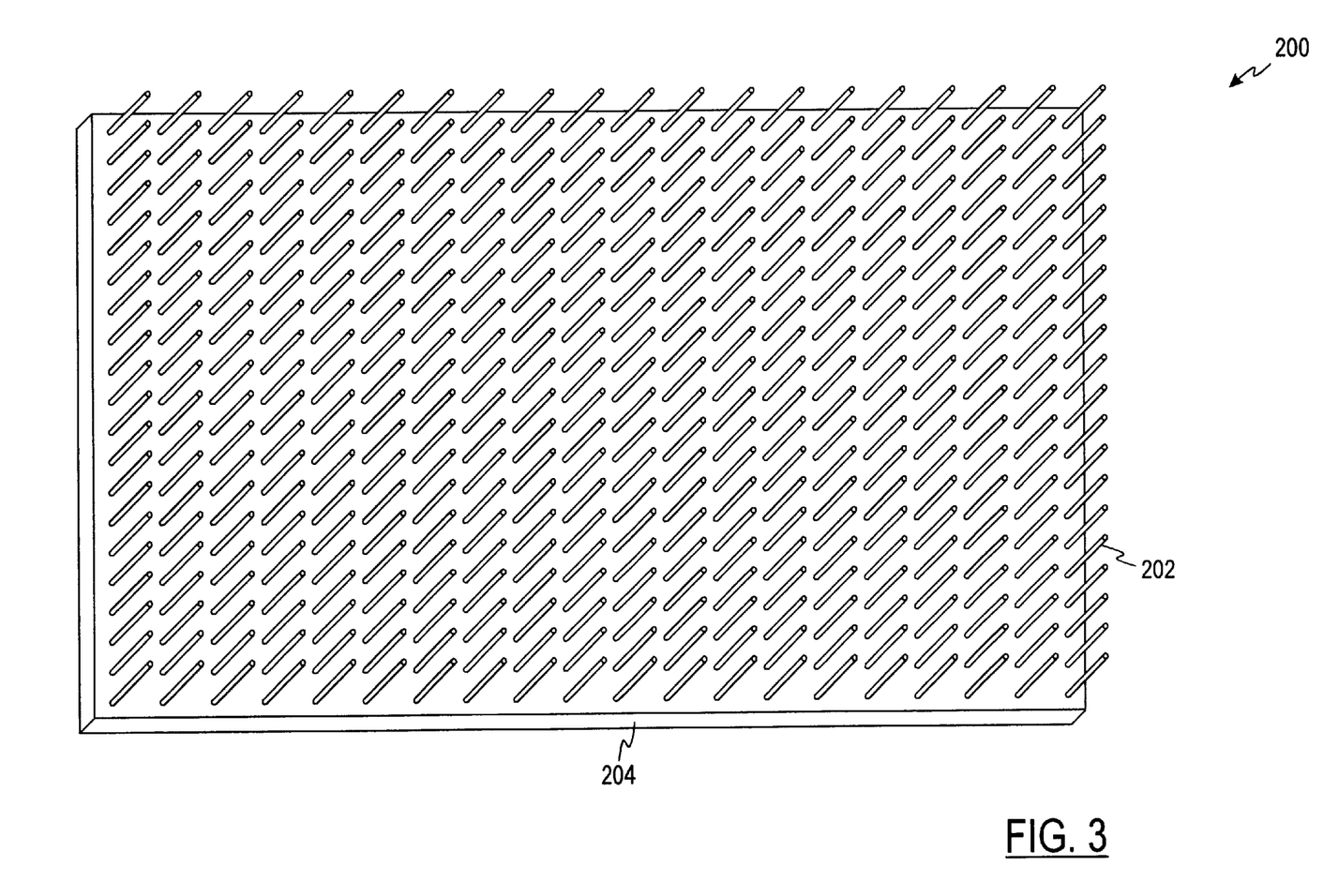
FIG. 3 is a perspective view of a microneedle patch according to one embodiment of the present invention.

Referring now to FIG. 3, a hollow microneedle patch 200 according to one embodiment of the present invention is illustrated. The microneedle patch 200 comprises a plurality of hollow microneedles 202 coupled to a test chamber 204. Blood is moved through each of the plurality of microneedles 202 by capillary action to the test chamber 204. In the illustrated embodiment of the present invention, the plurality of hollow microneedles 202 are arranged in a twenty by twenty array so that the microneedle patch 200 includes four hundred hollow microneedles 202. The microneedle patch 200 is used to lance a user's skin and to harvest a sample of blood. Essentially, the microneedle patch 200 integrates the prior art test sensor 102 and the lance 120 (discussed in conjunction with FIGS. 1 and 2) into a single unit.

Each microneedle penetrates the skin to a depth of about two-hundredths of an inch (0.005 inch). The microneedles 202 extend below the surface of the skin a distance sufficient to collect a sample of blood from the outermost layer of capillaries. The skin's outer layer, called the stratum corneum, does not contain any nerve endings. The first extensive nerve layer is disposed below the outermost layer of capillaries. Because each of the microneedles 202 do not contact any nerves, the lancing of the skin and the collection of blood is essentially painless. Further, because the lacerations created in the skin are much smaller that those created by a conventional lance, the risk of infection is lessened and the healing of the lacerations is expedited. The precise dimensions of the microneedles 202 and the microneedle 200 patch are a function of several variables including the amount of blood to be harvested and the type of blood glucose analysis to be used in conjunction with the microneedle patch 200.

Figure 4:
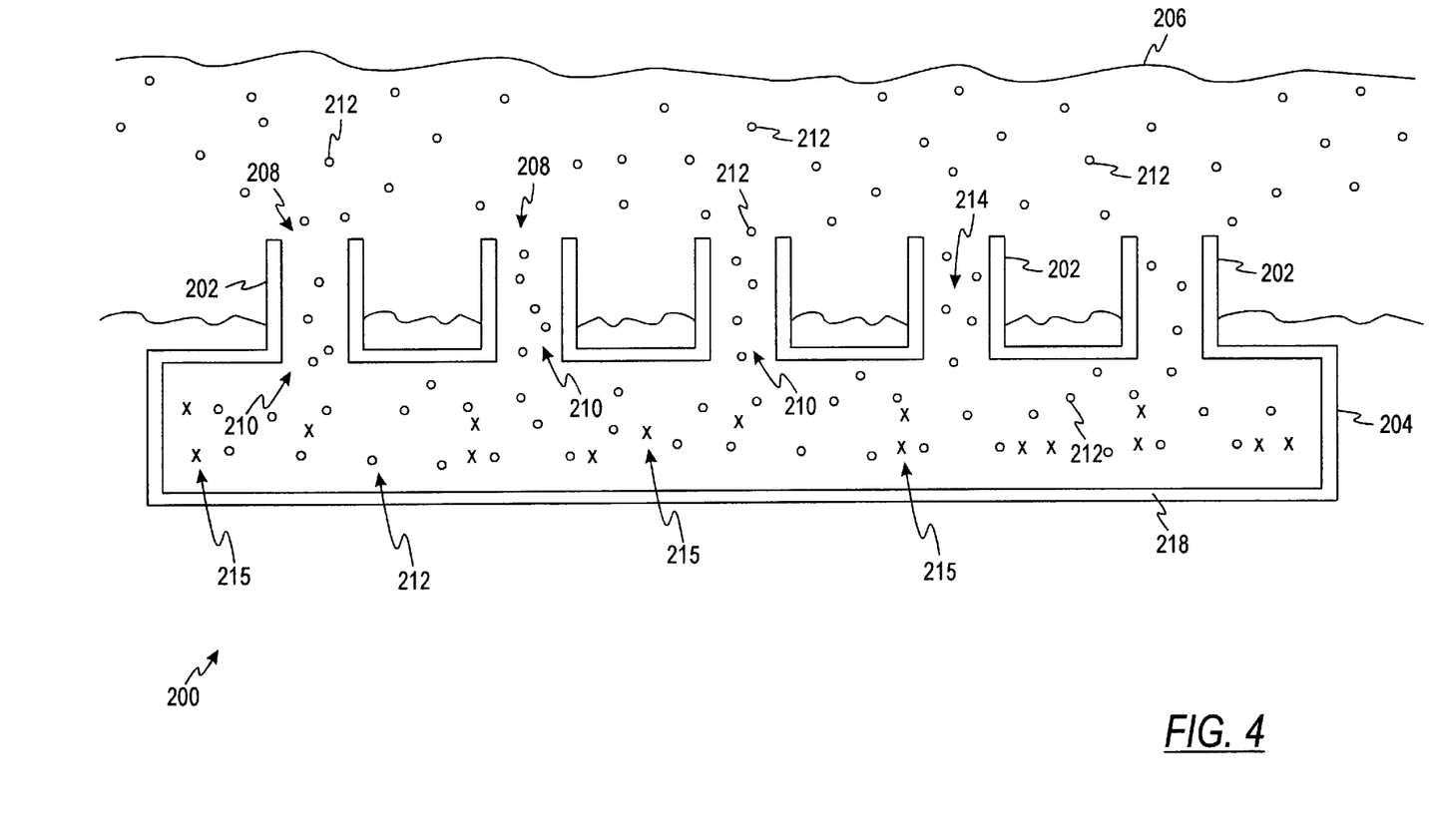
FIG. 4 is a cross-sectional view of the embodiment of the microneedle patch illustrated in FIG. 3.
Figure 5:
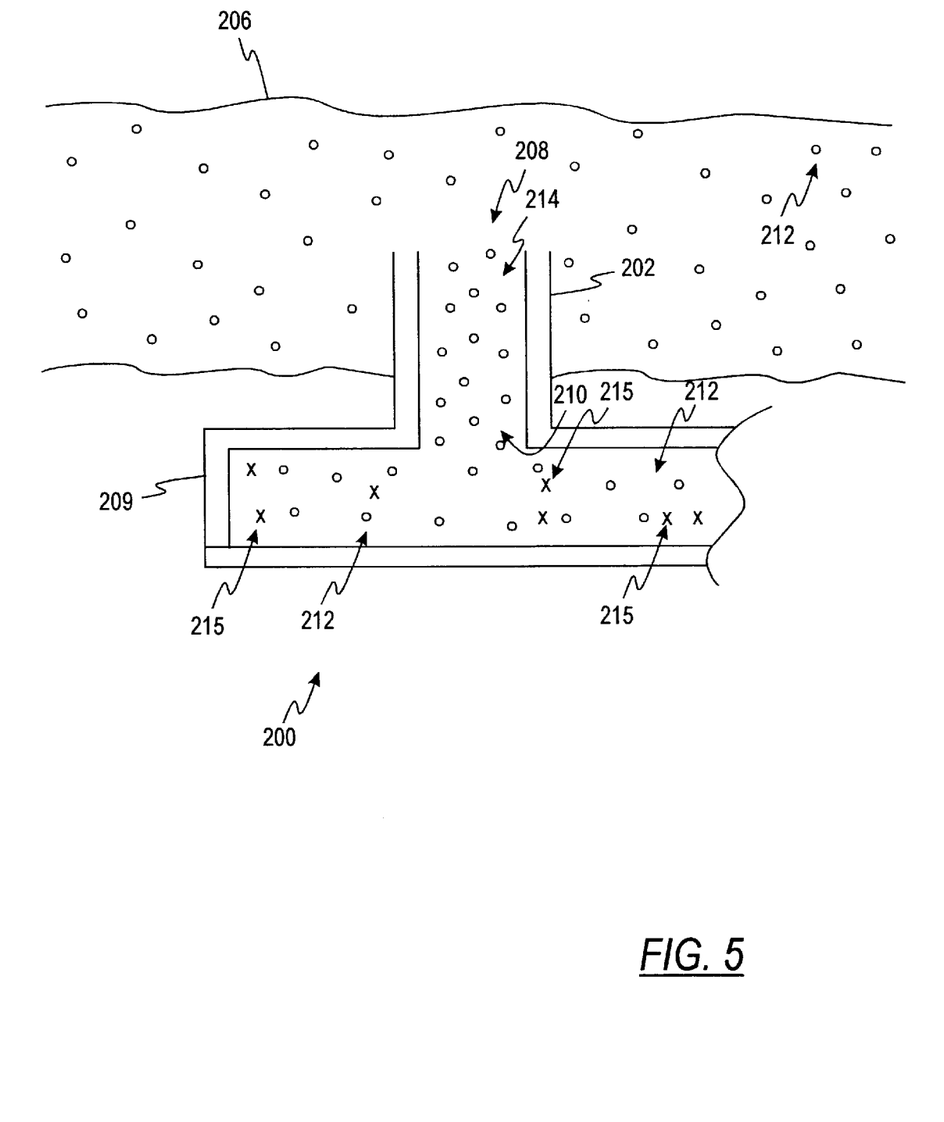
FIG. 5 is another cross-sectional view of the embodiment of the microneedle patch illustrated in FIG. 3.

Referring now to FIGS. 4 and 5, the microneedle patch 200 is illustrated pressed onto a user's skin 206 causing each of the microneedles 202 to penetrate the skin 206. Each of the microneedles 202 are hollow and have a collection point 208 and an outlet 210. The outlet 210 of each microneedle 202 is coupled to the test chamber 204. After penetrating the skin 206, blood 212 is collected though the collection point 208 of each of the microneedles 202. The blood 212 is moved though an interior 214 of the hollow microneedles 202 by capillary action to the test chamber 204. The requisite volume of blood 212 necessary for accurate testing is dependent on the type of glucose analysis employed. For example, the applicant has found that at least approximately one micro-liter of blood 212 is necessary to employ electrochemical analysis to determine the blood glucose concentration. Each of the plurality of microneedles 202 draws a portion of the requisite volume of blood 212 into the test chamber 204 where the analysis occurs.

A reagent 215 is incorporated in the test chamber 204 of the microneedle patch 200. Once blood is moved into the test chamber 204, the glucose in the blood 212 reacts with the reagent 215 in the test chamber 204 to produce a detectable signal. That signal is then measured by a sensor which can measure the concentration of the glucose in the blood 212 based on the signal. The specific reagent 215 incorporated into the test chamber 204 is a function of the type of sensing employed to determine the concentration of glucose in the blood 212.

In operation, a user can measure the concentration of the user's blood by pressing the microneedle patch 200 onto the user's skin. Each of the microneedles 202 lances the skin 206. A quantity of blood 212 is moved by capillary action from the collection point 208 of each microneedle 202 to the test chamber 204. The glucose in the blood 212 reacts with a reagent 215 incorporated into the test chamber 204 producing a signal indicative of the blood glucose concentration. That signal is then measured with an appropriate sensor in a blood glucose analyzer to determine the concentration of glucose in the user's blood. Once the blood glucose analyzer measures the signal produced by the reaction, the microneedle patch 200 can be discarded.

An advantage to the use of the microneedle patch 200 is that blood never comes into contact with the blood glucose analyzer. Therefore, in addition to self-testing, the microneedle patch 200 may be used at a clinical level because cross-contamination is not an issue. For example, a doctor may use a single blood glucose analyzer to test the blood glucose concentration for that doctor's patients. One microneedle patch 200 would be used for each patient. The microneedle patch is pressed onto the patient's skin and the signal produced by the reaction within the microneedle patch 200 is read by a blood glucose analyzer which never contacts the patient's blood. The blood glucose analyzer can be used again while the used microneedle patch 200, containing the sample of blood, is discarded.

Figure 6:
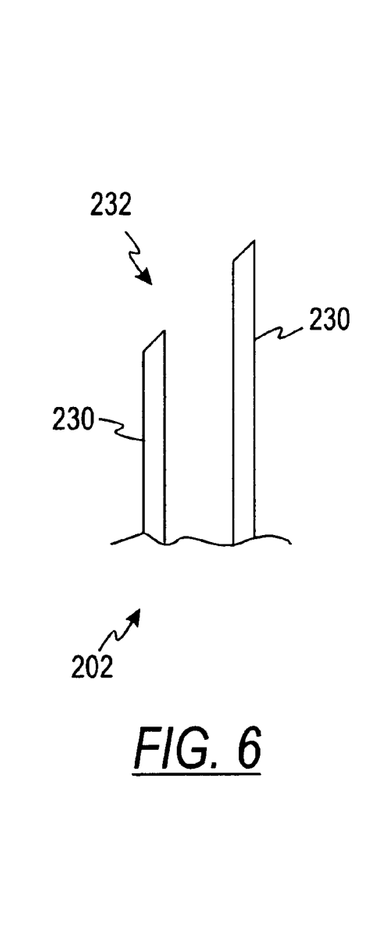
FIG. 6 is a collection point of a microneedle according to a second alternative embodiment of the present invention.
Figure 7:
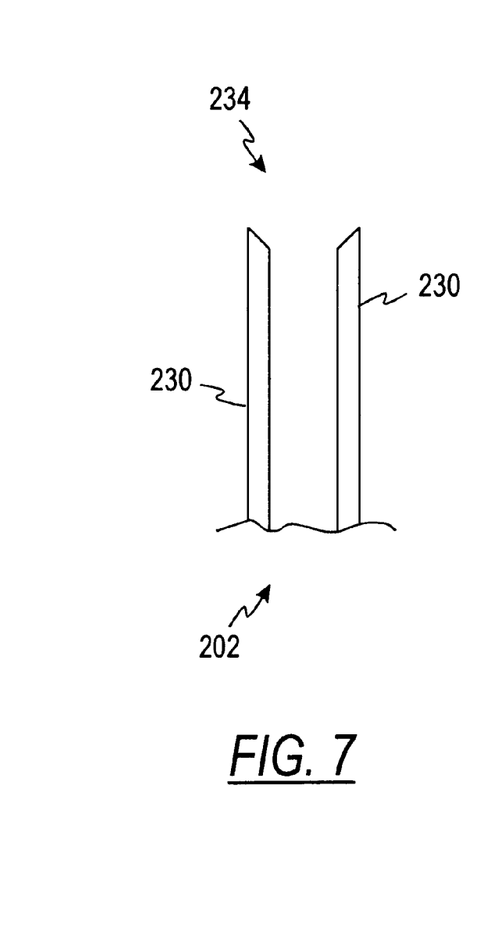
FIG. 7 is a collection point of a microneedle according to a third alternative embodiment of the present invention.
Figure 8:
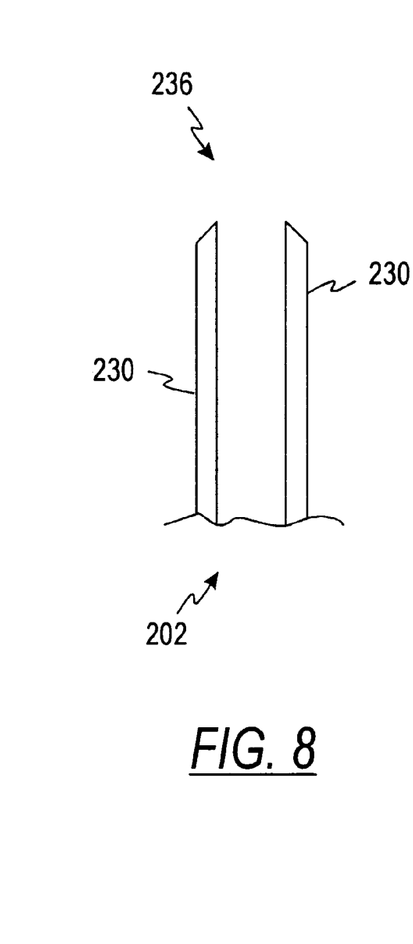
FIG. 8 is a collection point of a microneedle according to a forth alternative embodiment of the present invention.

Referring to FIGS. 6, 7 and 8, three alternative embodiments of the collection point of each microneedle 202 is illustrated. Each microneedle 202 of the present invention is generally shaped as a hollow cylinder having cylindrical walls 230. In FIG. 6, the collection point of the microneedle 202 is an angled collection point 232. A plane parallel to the angled collection point 232 is disposed at an angle relative to the longitudinal axis of the microneedle 202.

In another alternative embodiment, the microneedle 202 has a generally concave collection point 234 as illustrated in FIG. 7. The generally cylindrical walls 230 of the microneedle 202 are formed upwardly sloping radially away from the longitudinal axis of the microneedle 202 at the collection point 234.

In still another alternative embodiment, the microneedle 202 has a generally convex collection point 236 is illustrated in FIG. 8. In the embodiment illustrated in FIG. 8, the generally cylindrical walls 230 of the microneedles 202 are formed downwardly sloping radially away from the longitudinal axis of the microneedle 202 at the collection point 236. The shape of the alternative embodiments of the collections points illustrated in FIGS. 6–8 reduces surface tension at the collection point of the microneedle 202 thus facilitating the movement of blood from the collection point through the hollow microneedle 202 to the test chamber 104.

Colorimetric analysis is one type of analysis that can be utilized with the microneedle patch 200 of the present invention. The reaction of the glucose and a specific reagent produces a change in color, or a colorimetric reaction, which is indicative of the amount of glucose in the blood. That color change can be compared to a color chart, wherein the colors on the color chart were obtained using blood having a known glucose concentration, to determine the blood glucose concentration. The color change in the test chamber 204 caused by the reaction of the glucose and the reagent 215 can be read with a spectrophotometric instrument incorporated into a glucose monitoring device for use with the patch 200. In such an embodiment where colorimertic sensing is employed, a back side 218 (FIG. 4) of the test sensor 204 may be transparent allowing the glucose monitoring device to optically detect the color change.

Alternatively, electrochemical analysis is another type of analysis which may be utilized in conjunction with the microneedle patch 200 of present invention to determine the concentration of glucose in a user's blood. In such an embodiment, the test chamber 104 includes a pair of electrodes. In electrochemical analysis, the change in current across the electrodes caused by the reaction of the glucose and the reagent is indicative of the concentration of the glucose in the blood. The reaction of the glucose and the reagent creates an oxidation current at the electrode which is directly proportional to the user's blood glucose concentration. This current can be measured by an appropriate sensor implemented in an glucose monitoring device for use with the patch 200. The glucose monitoring device can then communicate to the user the blood glucose concentration. Both calorimetric and electrochemical testing systems are described in detail by commonly-owned U.S. Pat. No. 5,723,284 entitled "Control Solution and Method for Testing the Performance of an Electrochemical Device for Determining the Concentration of an Analyte in Blood" which is incorporated herein by reference in its entirety.

Figure 9:
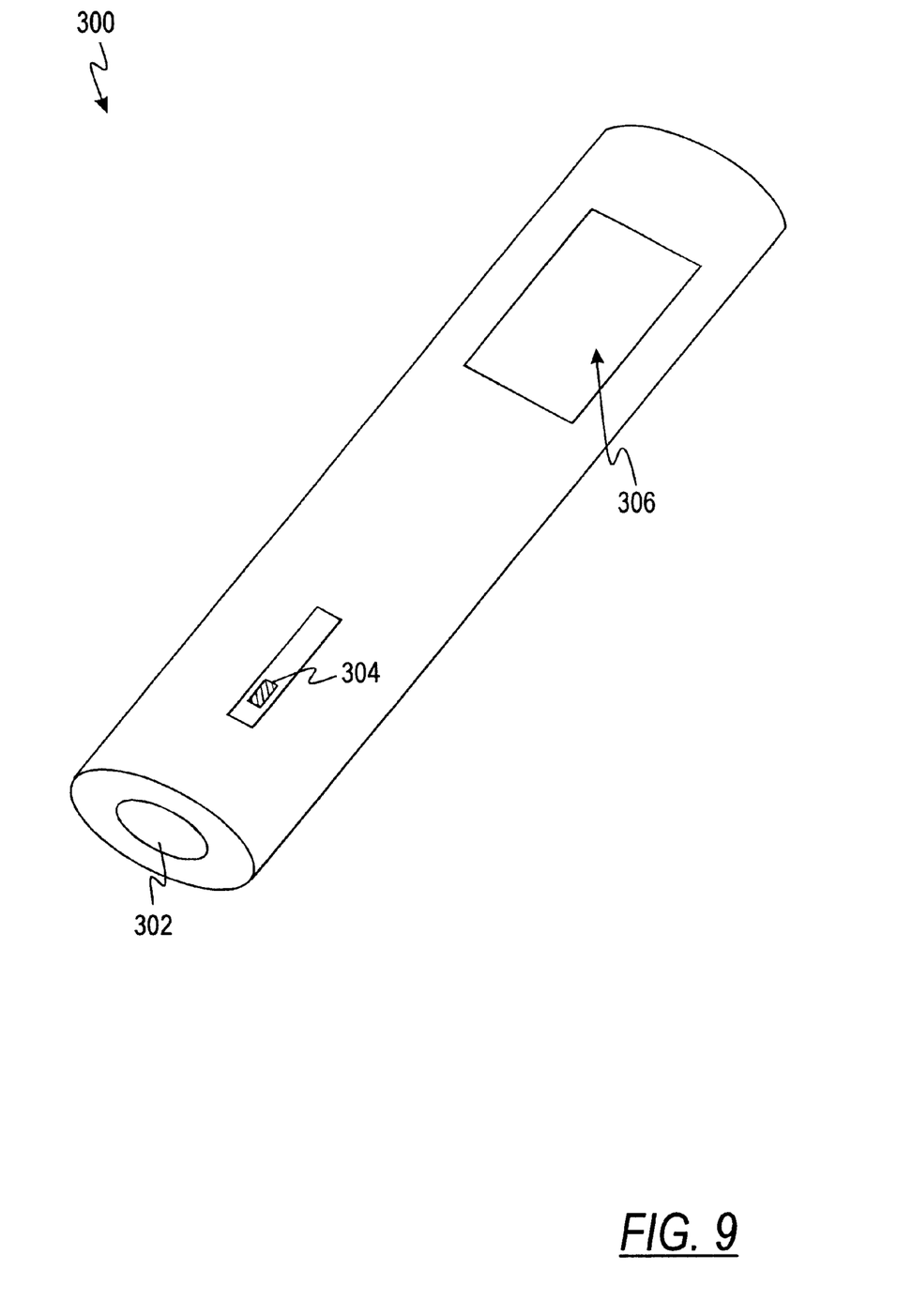
FIG. 9 is an embodiment of a blood glucose monitoring device for use in conjunction with a microneedle patch according to a sixth alternative embodiment of the present invention.

Referring now to FIG. 9, a glucose monitoring device 300 having a calorimetric sensor (a spectrophotometric instrument) 302 which may used in conjunction with the microneedle array patch 200 is illustrated. The test chamber 204 of the microneedle array patch 200 contains appropriate reagents designed to react with glucose in a manner to produce a change in color indicative of the glucose concentration in the user's blood. The glucose monitoring device 300 having a colorimetric sensor 302 determines the glucose concentration and informs the user of the result. The monitoring device 300 is activated with a switch 304. After the microneedle array patch 200 is pressed onto the user's skin and the requisite amount of time has past for the reaction to occur, the monitoring device 300 is brought into close proximity to the microneedle array patch 200 to read the colorimetric signal produced by the reaction. The test chamber 204 has a transparent back cover 218 allowing the calorimetric sensor 302 in the monitoring device 300 to optically read the signal. The monitoring then determines the blood glucose concentration and communicates those results to the user via a display 306. The microneedle patch 200 can then be removed and discarded.

Figure 10:
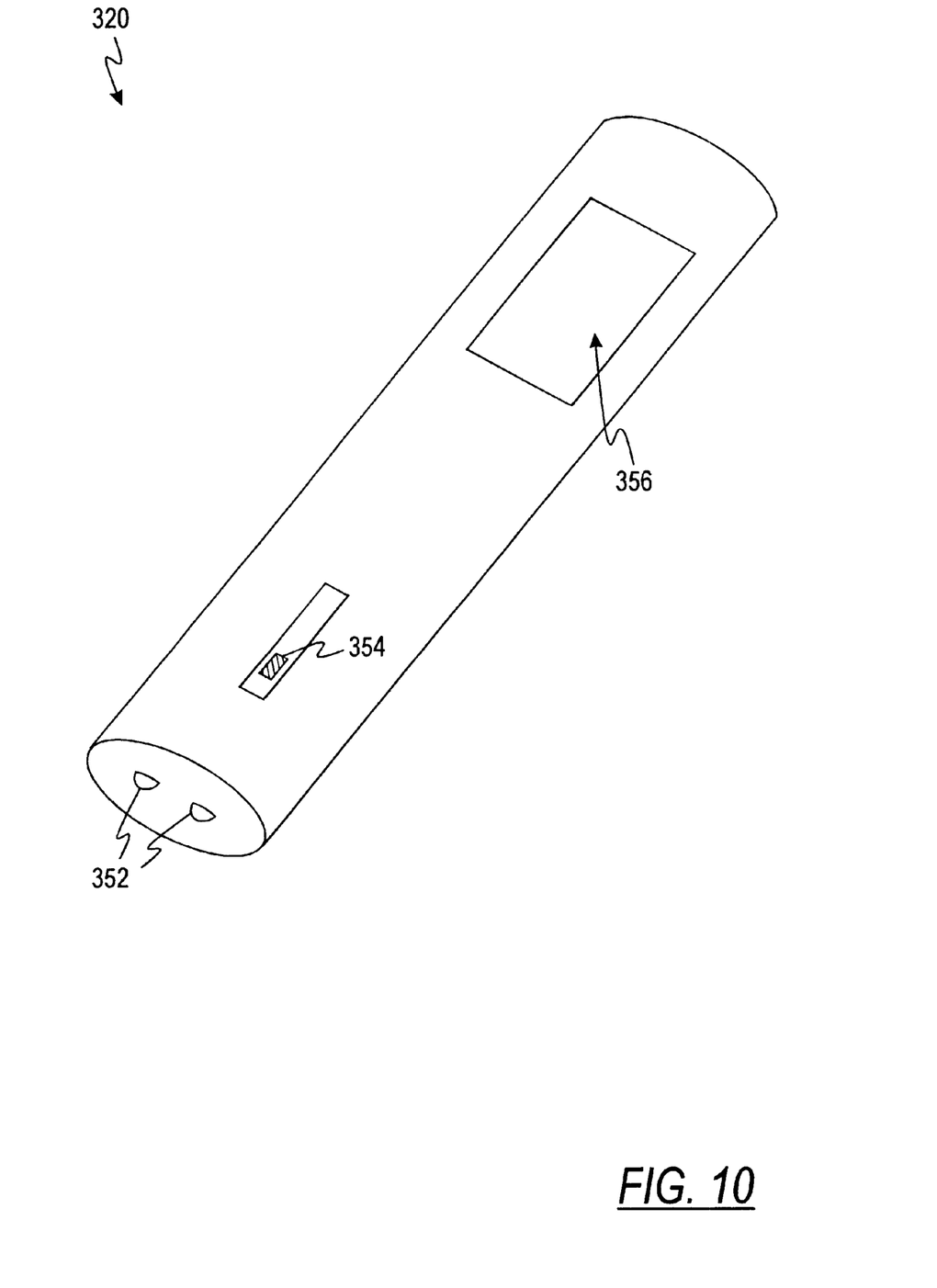
FIG. 10 is an embodiment of a blood glucose monitoring device for use in conjunction with a microneedle patch according to a seventh alternative embodiment of the present invention.

Alternatively, electrochemical sensing can be employed in conjunction with the microneedle array path of the present invention. FIG. 10 illustrates a suitable monitoring device 320 which can be used in conjunction with an embodiment of the microneedle patch 200 designed for electrochemical sensing. The embodiment of the microneedle patch 200 designed for electrochemical sensing contains a pair of electrodes 353. The blood glucose monitoring device 320 contains a pair of corresponding electrodes 352 (shown in FIG. 10). The blood glucose monitoring device 350 is activated with a switch 354. Once the microneedle patch 200 is pressed onto a users skin and a requisite amount of time has passed for the electrochemical reaction to occur, the electrodes 352 of the monitoring device are bought into contact with the corresponding electrodes 353 on the microneedle patch 200. The results of the blood glucose analysis are communicated to the user via a display 356.

Figure 11:
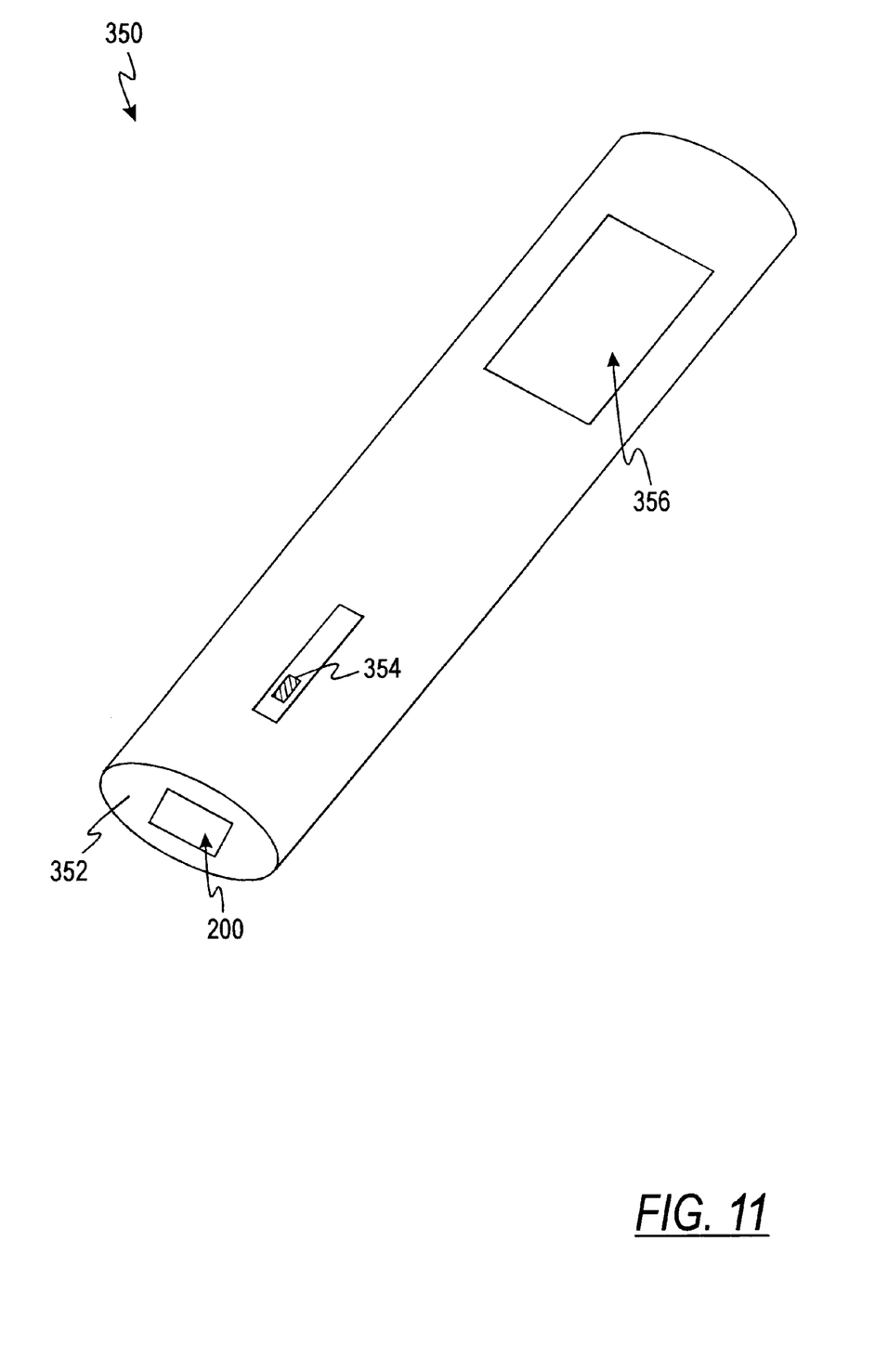
FIG. 11 is an embodiment of a blood glucose monitoring system according to an eighth alternative embodiment of the present invention.

Referring now to FIG. 11, another application of the microneedle patch 200 of the present invention is in an integrated blood glucose monitoring system 350 which integrates the microneedle array patch 200 and a blood glucose analyzer into a single instrument. The integrated blood glucose monitoring system contains a plurality of microneedle patches 200 and when activated moves a new microneedle patch 200 to the test end 352 of the system 350. In operation, a user would activate the system 350 with a switch 354. A new microneedle patch 200 is advanced to the test end 352 of the system 350. The user would then press the test end 352 of the system against the user's skin causing each of the microneedles 202 in the array of microneedles 202 to lance the user's skin and to harvest the blood sample.

Once the requisite blood sample has been obtained and the requisite time has elapsed for the reaction in the test chamber 204 of the microneedle patch 200 to occur, the blood glucose monitoring system 350 determines the blood glucose concentration and communicates the result to the user via a display 356. The used microneedle array patch is then ejected from the system 350. Both electrochemical sensing and colorimetric sensing as well as other types of blood glucose analysis may be implemented within the blood glucose monitoring system 350 of the present invention.

Figure 12:
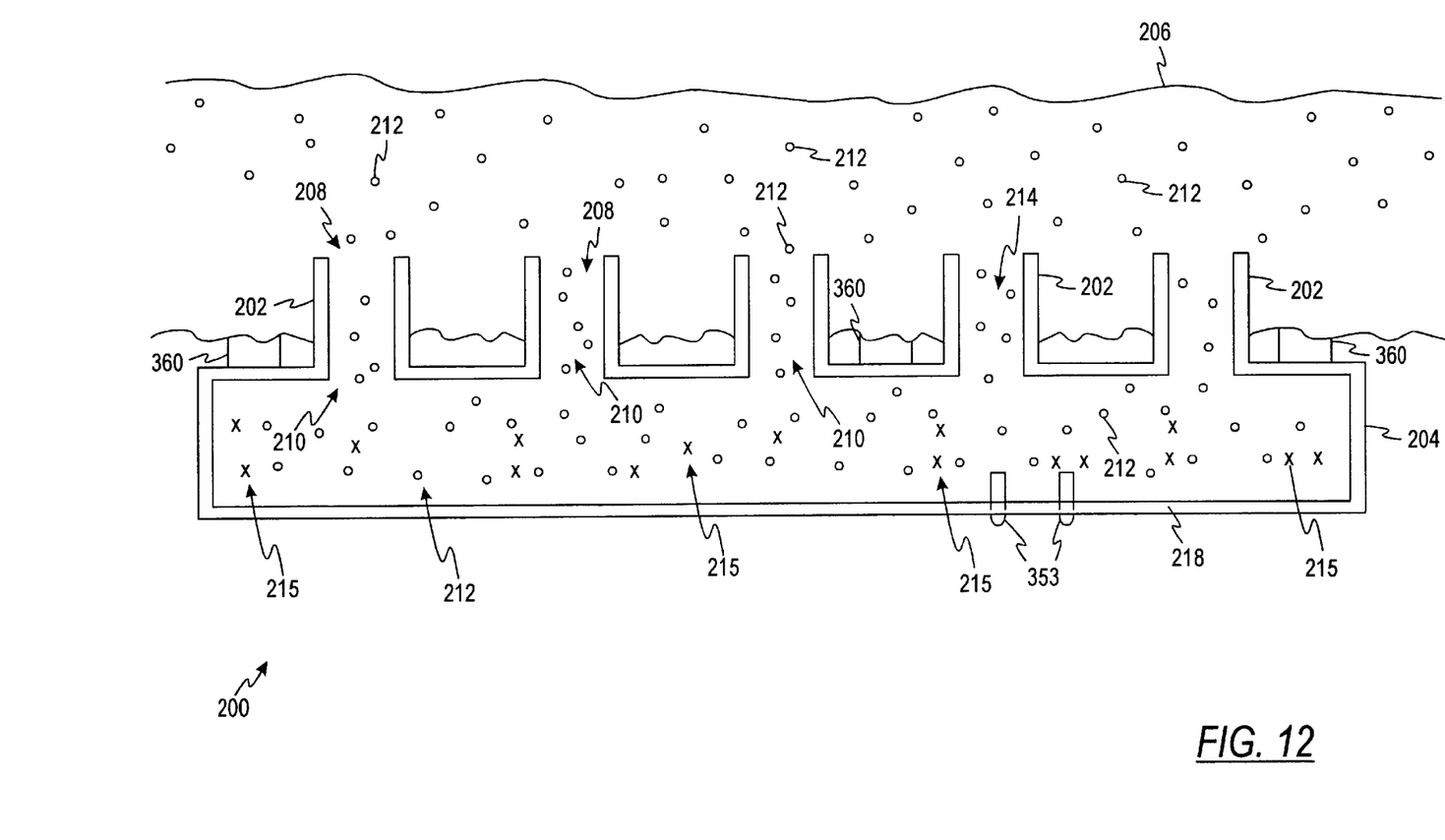
FIG. 12 is an embodiment of a blood glucose monitoring system according to a ninth alternative embodiment of the present invention.

Referring now to FIG. 12, another alternative embodiment of the present invention is illustrated wherein the microneedle patch 200 has an adhesive 360 disposed on an upper surface 362 of the microneedle patch 200 in an another alternative embodiment of the present invention. The adhesive 360 holds the microneedle patch 200 against a user's skin 206. The adhesive 360 is useful in an embodiment of the microneedle patch 200 wherein a longer period of time is required for the harvesting of the blood sample and then the occurrence of the reaction between the glucose in the blood and the reagent disposed in the test chamber 204. Also illustrated in FIG. 12 are the pair of electrodes 353 disposed in the test chamber 203.

While the invention is susceptible to various modifications and alternative forms, specific embodiments thereof have been shown by way of example in the drawings and will be described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

What is claimed is:

1. A test strip for use in the determination of the concentration of an a chemical in blood, comprising:

a plurality of microneedles, each microneedle being adapted to puncture skin and to draw blood, each microneedle having a generally cylindrical wall and a collection point, the collection point being adapted to receive blood and to direct blood to the test area, the cylindrical wall at the collection point being upwardly sloping in a direction moving radially away from the center of the microneedle; and a test area in fluid communication with the microneedles, the test area containing a reagent being adapted to produce a reaction indicative of the concentration of a chemical in blood.

2. The test strip of claim 1 wherein the reagent is adapted to produce a colorimetric reaction.

3. The test strip of claim 2 in combination with a colorimetric sensor.

4. The test strip of claim 1 wherein the reagent is adapted to produce an electrochemical reaction, the test strip further comprising a pair of electrodes coupled to the test area.

5. The test strip of claim 4 in combination with a sensor being adapted to measure a change in current across the electrodes.

6. The test strip of claim 1 wherein the chemical is glucose.

7. The test strip of claim 6 in combination with a sensor adapted to measure the concentration of glucose in the blood.

8. The test strip of claim 1 further comprising an adhesive disposed on the test area, the adhesive being adapted to adhere the test strip to skin.

9. The test strip of claim 1 wherein each microneedle has a length of at least about 0.005 inch.

10. The test strip of claim 1 wherein each microneedle is hollow.

11. The test strip of claim 1 wherein the plurality of microneedles is a twenty by twenty microneedle array.

12. A blood chemical monitoring system for monitoring the concentration of chemical in blood, the system comprising:
- a test chamber having a top and a bottom, the test chamber containing a reagent;
- an array of hollow microneedles, each of the hollow microneedles being adapted to draw blood, each of the microneedles containing an inlet and an outlet, said inlet being adapted to puncture skin, the outlet being in fluid communication with the test chamber, each microneedle having a generally cylindrical wall, the cylindrical wall at the inlet being upwardly sloping in a direction moving radially away from the center of the microneedle at the collection point; and
- a sensor for determining the concentration of a chemical in the blood.

13. The system of claim 12 wherein the reagent is adapted to produce a colorimetric reaction and the sensor is a colorimetric sensor.

14. The system of claim 12 wherein the bottom of the test chamber is transparent.

15. The system of claim 12 wherein the test chamber includes a pair of electrodes and the reagent is adapted to produce an electrochemical reaction, the sensor being adapted to measure a change in current across the electrodes.

16. The system of claim 12 wherein the chemical is glucose.

17. The system of claim 12 futher comprising an adhesive disposed on the top of the test chamber, the adhesive being adapted to adhere the test chamber to skin.

18. The system of claim 12 wherein each hollow microneedle has a length of at least about 0.005 inch.

19. The system of claim 12 wherein the array of hollow microneedles is a twenty by twenty hollow microneedle array.

* * * * *